US011666689B2

(12) United States Patent  
Kumar et al.

(10) Patent No.: US 11,666,689 B2  
(45) Date of Patent: *Jun. 6, 2023

(54) AUTOMATED COMPRESSION NURSING AND PUMPING SYSTEM

(71) Applicant: LILU, INC., Brooklyn, NY (US)

(72) Inventors: Sujay Suresh Kumar, New York, NY (US); Adriana Catalina Vazquez Ortiz, New York, NY (US)

(73) Assignee: Lilu, Inc., New York, NY (US)

( * ) Notice: Subject to any disclaimer, the term of this patent is extended or adjusted under 35 U.S.C. 154(b) by 374 days.

This patent is subject to a terminal disclaimer.

(21) Appl. No.: 16/924,671

(22) Filed: Jul. 9, 2020

(65) Prior Publication Data

US 2020/0337938 A1 Oct. 29, 2020

Related U.S. Application Data

(63) Continuation-in-part of application No. 16/424,766, filed on May 29, 2019, now Pat. No. 10,758,653, (Continued)

(51) Int. Cl.  
*A61M 1/06* (2006.01)  
*A41C 3/04* (2006.01)  
(Continued)

(52) U.S. Cl.  
CPC ............ *A61M 1/0697* (2021.05); *A41C 3/04* (2013.01); *A61M 1/067* (2021.05); *A41C 3/105* (2013.01);  
(Continued)

(58) Field of Classification Search  
CPC .......... A41C 3/04; A61H 9/0078; A61M 1/06; A61M 1/062; A61M 1/064; A61M 1/066  
See application file for complete search history.

(56) References Cited

U.S. PATENT DOCUMENTS

| 4,551,874 A | 11/1985 | Matsumara et al. |
| 5,885,246 A | 3/1999 | Ford |

(Continued)

FOREIGN PATENT DOCUMENTS

| CN | 1244808 C | 2/2000 |
| CN | 1799436 C | 7/2006 |

(Continued)

OTHER PUBLICATIONS

Office Action in Application No. CN2017112925967.  
(Continued)

*Primary Examiner* — William R Carpenter  
(74) *Attorney, Agent, or Firm* — Leydig, Voit & Mayer, Ltd.

(57) ABSTRACT

A system for hands-free nursing and breast pumping includes a breast compression device with a plurality of thermoformed fluid bladders designed to fit adjustably against each breast and inflate and deflate with minimal power requirements. The compression device and its controller fit inside of a nursing garment designed to receive the device and controller for optimal compression. The nursing garment and the compression device have openings over the nipples so that a breast pump flange can be inserted through them and used in a typical manner for the extraction of breast milk, thus increasing the amount of milk expressed.

9 Claims, 12 Drawing Sheets

Related U.S. Application Data which is a continuation-in-part of application No. 15/598,050, filed on May 17, 2017, now abandoned, which is a continuation of application No. 15/373,752, filed on Dec. 9, 2016, now abandoned.

(60) Provisional application No. 62/419,747, filed on Nov. 9, 2016.

(51) Int. Cl.
*A61H 9/00* (2006.01)
*A41C 3/10* (2006.01)

(52) U.S. Cl.
CPC .... *A61H 9/0078* (2013.01); *A61H 2201/0134* (2013.01); *A61H 2201/1207* (2013.01); *A61H 2201/165* (2013.01); *A61H 2201/1621* (2013.01); *A61H 2201/5007* (2013.01); *A61H 2205/082* (2013.01)

(56) References Cited

U.S. PATENT DOCUMENTS

| | | |
|---|---|---|
| 6,273,868 B1 | 8/2001 | Nordvik |
| 6,383,164 B1 | 5/2002 | Johansen et al. |
| 10,758,653 B2 * | 9/2020 | Kumar ............... A61H 9/0057 |
| 2005/0234370 A1 | 10/2005 | Beal et al. |
| 2006/0106334 A1 * | 5/2006 | Jordan ............... A61M 1/062 |
| | | 604/74 |
| 2008/0039781 A1 | 2/2008 | Bjorge |
| 2014/0378946 A1 | 12/2014 | Thompson et al. |
| 2015/0065994 A1 | 3/2015 | Fridman et al. |
| 2017/0112983 A1 | 4/2017 | Thorne et al. |

FOREIGN PATENT DOCUMENTS

| | | |
|---|---|---|
| CN | 205924425 U | 2/2017 |
| KR | 2020130002774 U | 5/2013 |

OTHER PUBLICATIONS

First Search Report in CN Application 2017112925967, filed Dec. 8, 2017.
Second Search Report in CN Application 2017112925967, filed Dec. 8, 2017.
U.S. Appl. No. 15/598,050, filed May 17, 2017.
U.S. Appl. No. 16/424,766, filed May 29, 2019.

* cited by examiner

AUTOMATED COMPRESSION NURSING AND PUMPING SYSTEM

CROSS-REFERENCE TO RELATED APPLICATIONS

The present application claims the benefit of U.S. Utility patent application Ser. No. 16/424,766, which is a continuation-in-part of U.S. Utility patent application Ser. No. 15/598,050, filed May 17, 2017, which is a continuation of U.S. Utility patent application Ser. No. 15/373,752, filed Dec. 9, 2016, which claims the benefit of U.S. Provisional Patent Application 62/419,747, filed Nov. 9, 2016. The contents of those applications are hereby incorporated by reference.

BACKGROUND

It is known that manual breast massage increases the amount of milk expressed in a breastfeeding session (Bowles, B. C. (2011). Breast Massage: A "Handy" Multipurpose Tool to Promote Breastfeeding Success. *Clinical Lactation*, 2(4), 21-24.). Health benefits of compression massage during breastfeeding or breast pumping include preventing and relieving mastitis, plugged ducts, and engorgement (Witt, A. M. et. al. (2016). Therapeutic Breast Massage in Lactation for the Management of Engorgement, Plugged Ducts, and Mastitis. *Journal of Human Lactation*, 32(1), 123-31.). When combined with electric pumping, manual massage both increased milk production (Morton, J. et. al. (2009). *Journal of Perinatology*, 29, 757-64.) and caloric content (Morton, J. et. al. (2012). *Journal of Perinatology*, 32, 791-96.) for preterm infants. The benefit is not limited to preterm infants, however. Compression stimuli around the areola increases breast pump efficiency more generally by stimulating the release of necessary hormones (Alekseev, N. P. et. al. (1998). Compression stimuli increase the efficacy of breast pump function. *European Journal of Obstetrics & Gynecology and Reproductive Biology*, 77(2), 131-39.). While manual massage has been used for centuries, the ability to pump efficiently hands-free would greatly improve the modern mother's productivity.

Breast compressions is also widely accepted as an effective post-surgery treatment for breast cancer related lymphedema (BCRL). One of the major important long-term complications of breast cancer treatment is lymphedema, a condition associated with adverse physical and psychosocial consequences. The major manifestation of lymphedema (LE) is chronic swelling, which causes discomfort, loss of function, and morbidity due to lymphatic impairment. Treatment of lymphedema is time consuming and expensive, and an early multidisciplinary approach is required to diagnose, treat, and prevent recurrence. Breast compression therapy has been proven to be effective in reducing swelling at the site of residual fluid, and maintaining positive postsurgical outcomes. The use of carefully selected compression garments is an effective, simple, and cheap treatment for BCRL. *Compression therapy in breast cancer-related lymphedema: A randomized, controlled comparative study of relation between volume and interface pressure changes*, by Rita Hansdorfer-Korzon, Jacek Teodorczyk, Agnieszka Gruszecka, Piotr Lass.

There are existing systems that combine hands-free compression and pumping. U.S. Pat. No. 6,213,840 B1, for example, discloses a simple hands-free bra that supports a breast pump system. It does not, however, address the need for compression. Some breast pumps have been designed to mimic manual compression, such as that described by the application US 2005/0234370 A1, which discloses that pressure is applied by a "plurality of opposing pairs of expression bellows." At least two patent applications describe hands-free compression systems to be used in conjunction with breast pumps using pneumatic modes of compression (US 2014/0378946 A1 and US 2015/0065994 A1). However, the prior art does not incorporate systems or methods that effectively mimic the best practices of manual compression, as indicated by research and expertise of lactation specialists, in an efficient device with low power requirements.

SUMMARY

The present invention addresses the needs in the prior art by providing rotating compression pressure across multiple areas of the breasts, more closely mimicking manual compression. The system and methods described herein further incorporate the existing research and existing expertise of lactation specialists to provide a controllable, hands-free compression and breast pumping system.

In particular, the system described herein provides hands-free expression of milk from human breasts in a rotating manner across multiple areas of the breast to mimic natural manual compression. The system comprises a compression device, a controller that controls the compression device, and a specialized garment for receiving the compression device, the controller and breast pump flanges. The compression device is comprised of a left and a right adjustable breast pad, each breast pad having a plurality of bladders whose inner surfaces comprise a plurality of ridges that perform massage effects on the breasts as the bladders are inflated and deflated by the controller. The compression device is actuated through fluid tubes that pass from the controller into the plurality of bladders of the compression device. The controller increases or decreases the pressure exerted by the compression device by increasing or decreasing the amount of fluid introduced into the compression device, which then determines how much the bladders inflate into the breast.

BRIEF DESCRIPTION OF THE DRAWINGS

The present invention will be more fully understood from the detailed description below taken in conjunction with the accompanying drawings, in which.

DETAILED DESCRIPTION

Certain embodiments will now be described to provide an overall understanding of the principles of the structure, function, manufacture, and use of the devices and methods herein disclosed. One or more examples of these embodiments are illustrated in the accompanying drawings, briefly described above.

Figure 1:
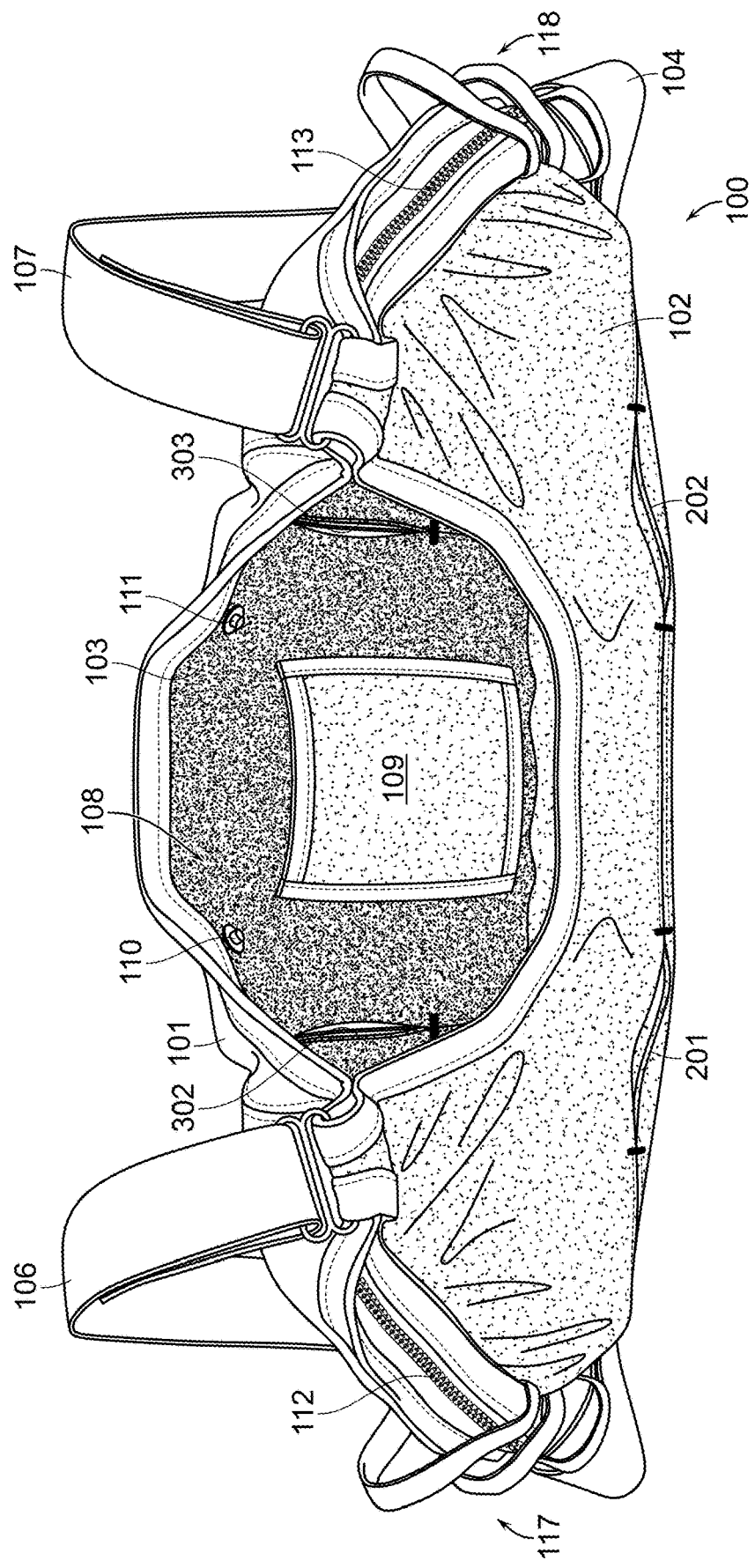
FIG. 1 is a top view of a garment that has been configured to accommodate a compression device and controller.
Figure 4:
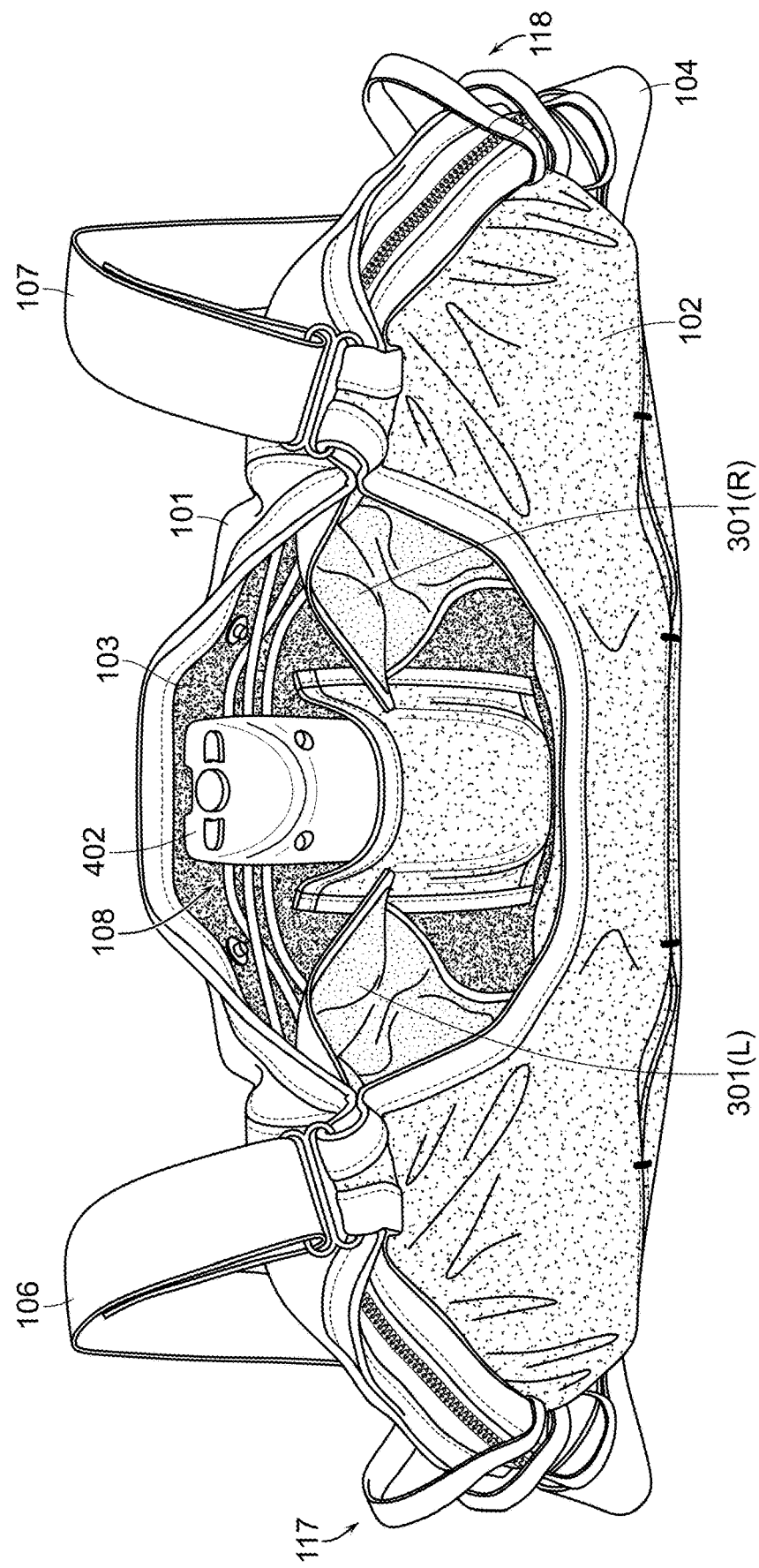
FIG. 4 is a top view of the garment with compression device and controller inside.

FIG. 1 is a top view of a garment [100], which has been configured to accommodate a compression device, a controller, and a breast pump. The garment comprises a bust cover comprising an outer layer [101], an inner layer [102] and a compression layer [103]; a torso band [104] binding the outer layer, inner layer and compression layer and having a closure means [105]; and a left [106] and right [107] shoulder strap connecting the bust cover to the torso band allowing the garment to be fastened in the back and worn as a bra. The combination of the inner layer [102] and compression layer [103] bound by the torso band [104] forms a pocket [108] for receiving the compression device [301]. FIG. 4 is a back top perspective view showing the compression device [301] and controller [402] within the pocket [108]. A holster [109] located on the compression layer [103] holds the controller [402] in place over the breasts when worn, and as will be described further herein, positioning the controller [402] as such within the garment helps stabilize the compression device so that adequate compression can occur in and around the cleavage area of the breasts. It will be noted that the controller is small enough to fit within the holster [109] in the garment [100], and that the structure of the compression device [301] is designed to require minimal amounts of pneumatic or hydraulic power from the controller.

Figure 5:
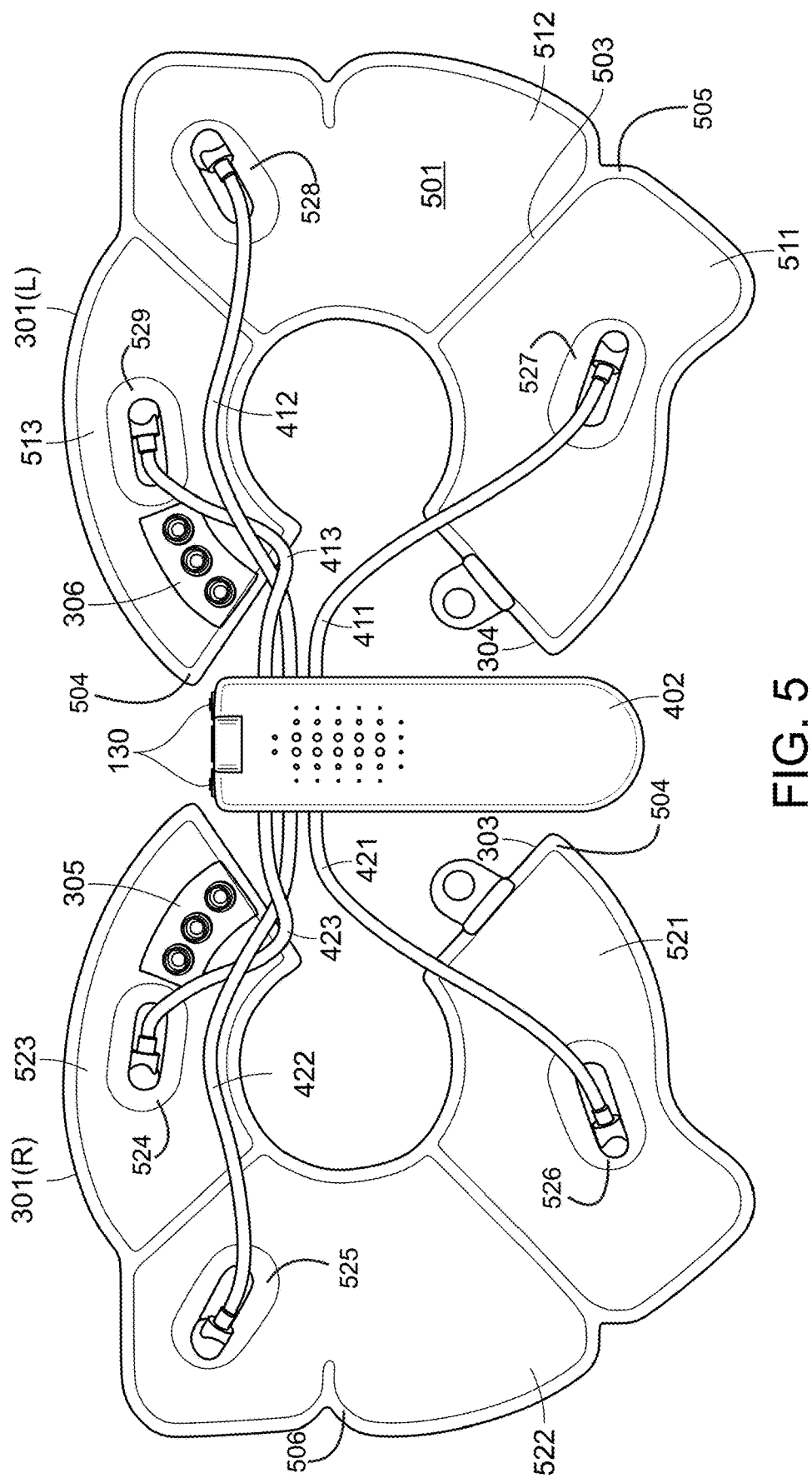
FIG. 5 is an anterior view of the compression device.
Figure 6:
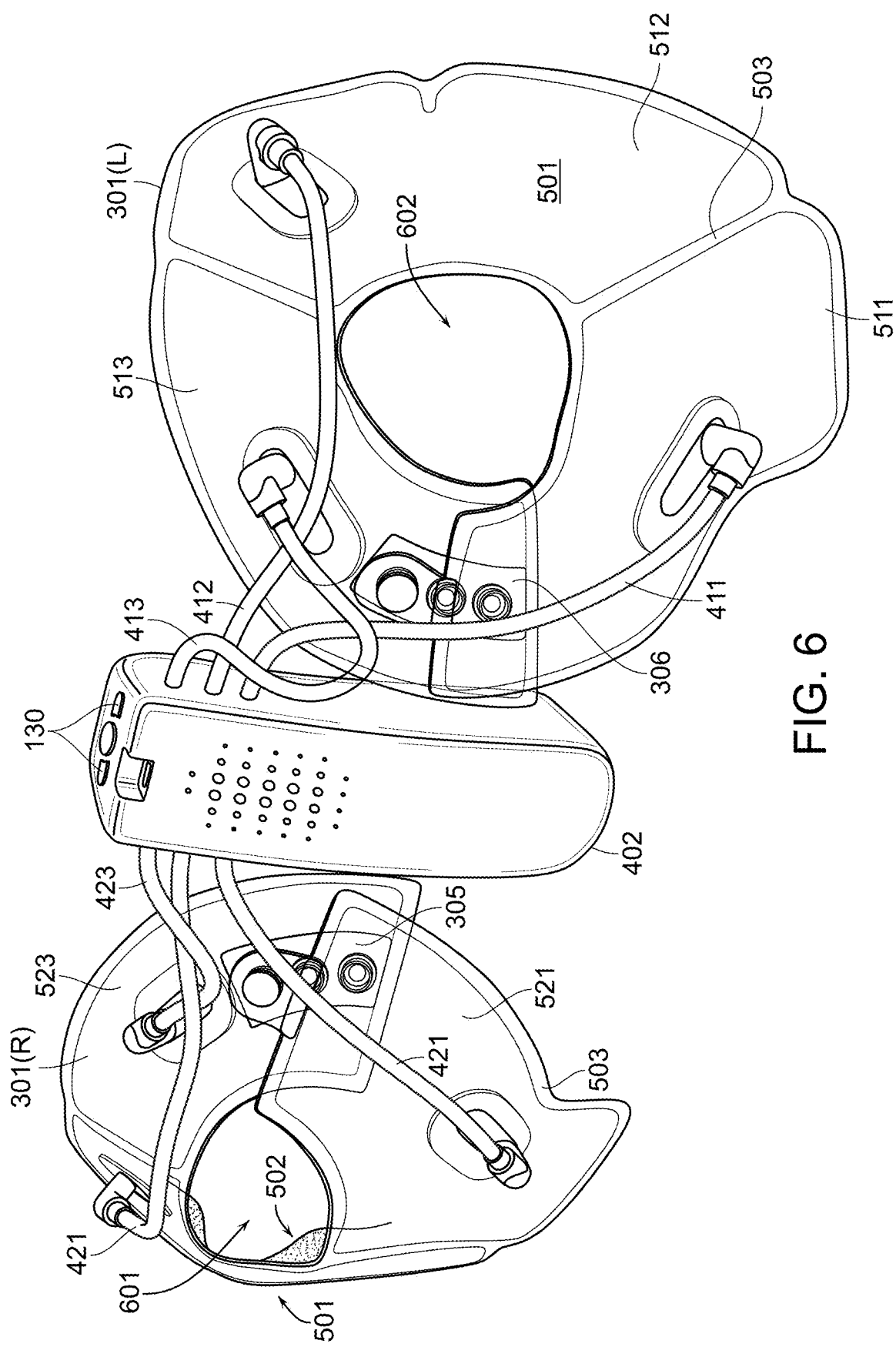
FIG. 6 is a perspective view of the compression device.

FIG. 5 and FIG. 6 are anterior and anterior perspective views of a compression device [301] and controller [402] suitable for use with garment [100]. The compression device is comprised of a left breast pad [301(L)] and a right breast pad [301(R)], each breast pad being a C-shaped pad with opening, and each breast pad comprising anterior [501] and posterior [502] sheets, which are sealed [503] together to form a plurality of fluid bladders sectors [511-513; 521-523], each bladder supplied with a fluid supply tube [411-413; 421-423] attached to fluid egress openings [524-529] at the anterior sheet [501]. Each fluid bladder is formed by the seal spanning the entire radius of the C-shaped pad, whereby the fluid bladders are sectors of the C-shaped pad. These fluid bladder sectors [511-513; 521-523] are inflated and deflated to perform pneumatic breast massage.

Figure 11:
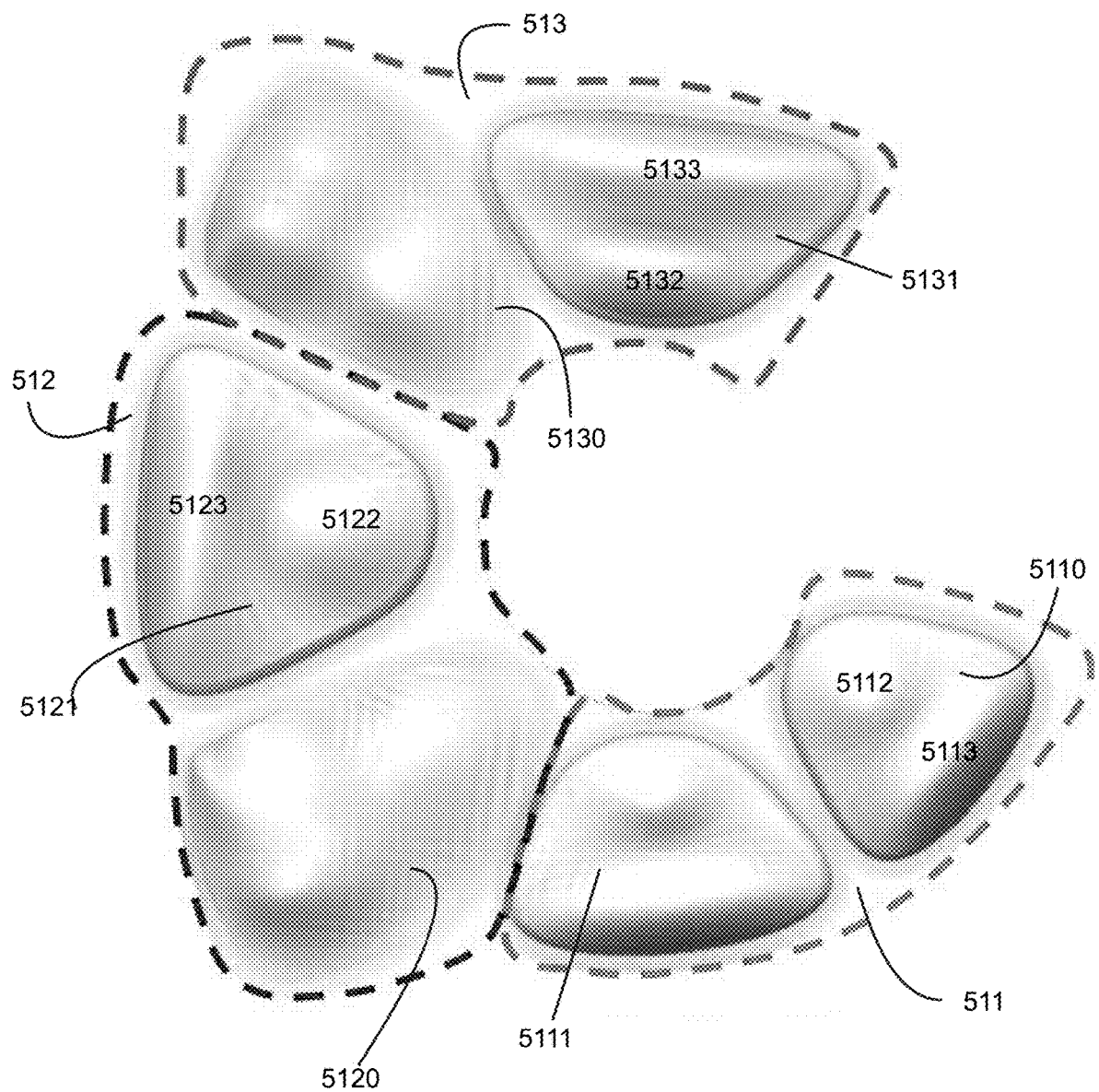
FIG. 11 is a plan view of a breast pad with shading to show topology of the ridges on the posterior sheet.

As shown in FIG. 5, the fluid bladders may have shapes that extend beyond the 'C' edge, to provide additional massage coverage. The optimal measurements for the C-shaped pad, which is adjustable to fit a wide span of breast sizes, are found to be approximately in the range of 220 sq·cm to 360 sq·cm with the diameter of the 'C' opening in the middle of the pad ranging from 3 to 10 cm. In the case of three fluid bladder sectors as depicted in FIG. 11, the shapes of the second and third bladders [512] and [513] extend beyond the 'C' edges, so that the surface area of the massage pads reach farther into the rear and base of the breast. In that case, the surface area the first bladder [511] is approximately in the range of 60 sq·cm to 100 sq·cm, the surface area of the second bladder [512] is approximately in the range of 90 sq·cm to 130 sq·cm, and the surface area of the third bladder [513] is approximately in the range of 90 sq·cm to 130 sq·cm. For example, the surface area of the first bladder could be 60 sq·cm, the surface area of the second bladder could be 90 sq·cm and the surface area of the third bladder 90 sq·cm for the smallest size bladders and 100 sq·cm, 130 sq·cm and 130 sq·cm respectively for the biggest size bladders.

Seals [503] are between 2.5 mm and 3 mm throughout each breast pad, thereby maximizing the coverage area of the inflatable bladders, while still remaining thick enough to withstand the pressure of repeated inflation without wear or rupture. Furthermore, seals should be shaped to distribute, rather than to focus, the direction of pressure from repeated inflation. Corners [504] at the edges of the C-shaped pads must be softened with a radius of curvature between 2 mm and 4 mm. When a seal separates fluid bladder sectors, such as the seal [505] between sectors [511] and [512], the seal is subject to inflation pressure from both directions, and the radius of curvature should be greater than 15 mm.

Figure 7:
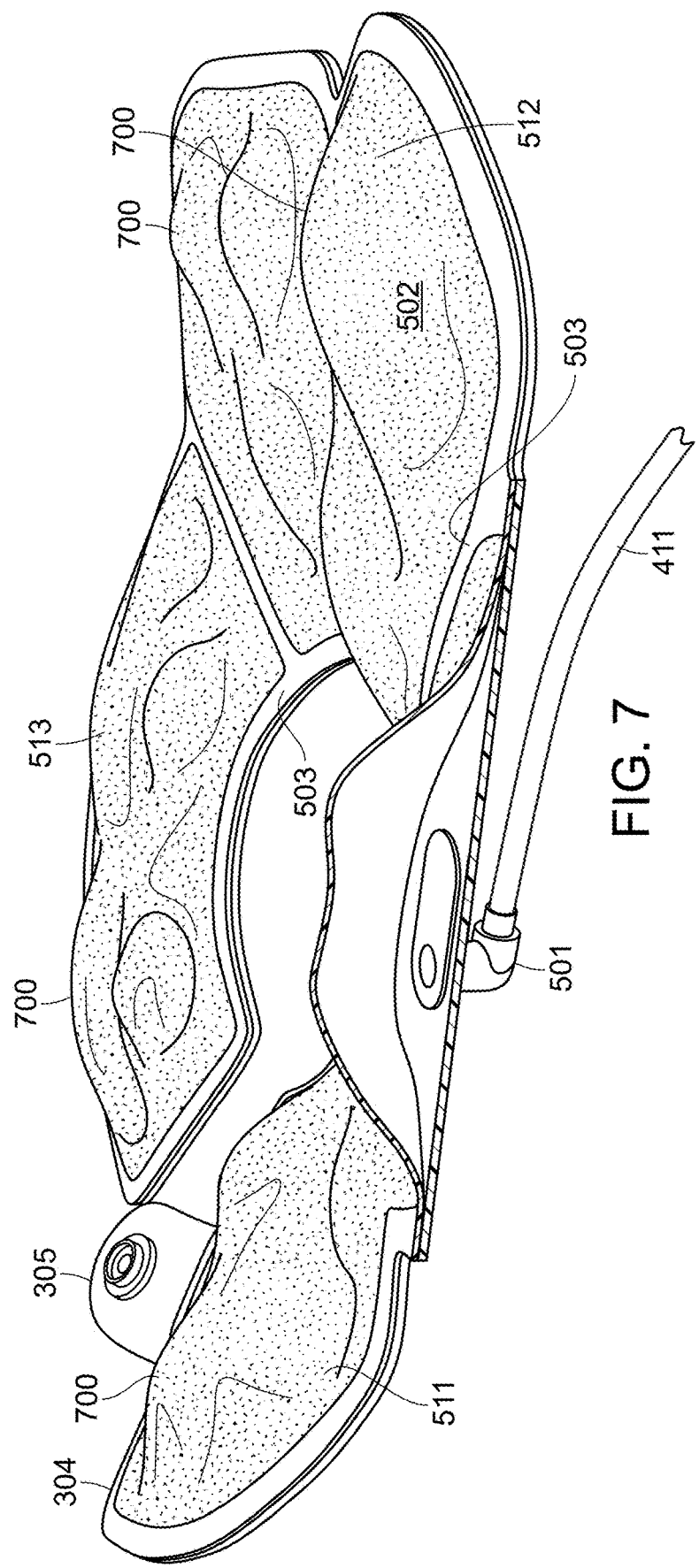
FIG. 7 is a side view of a breast pad of the compression device.

FIG. 7 is a side perspective view of a breast pad, partially opened to show the distinct anterior [501] and posterior [502] sheets, which are sealed [503] together to form the plurality of bladders [511-513]. Sheets of thermoplastic polyurethane (TPU) may be sealed, bonded, welded together, etc . . . , and are defined by their thickness and hardness, for instance, TPU 0.5 mm 90 A indicates that the TPU is 0.5 mm thick and the sheer hardness is 90 A. In order to ensure that posterior sheet [502] is inflated into the breast (instead of being pushed away from the breast), the inner, or posterior, sheet [502] should be thinner and less hard than the outer, or anterior, sheet [501]. This mechanism ensures that when the fluid bladders are inflated by introducing fluid through fluid egress openings [524-529], the outer sheet [501] offers more resistance to the pressure exerted by the fluid than the inner surface, causing the fluid bladders to inflate more in the inside of the pad than the outside. Thus, when the pads are worn against a lactating breast, the inflation of the fluid bladders is towards the breast, instead of away, thereby increasing the efficiency of the compression system.

Because the posterior [502] sheet faces the breast it is comprised of malleable ridges [700] that simulate fingertip like pressure and produce lactation massage effects as the bladders are inflated and deflated. Preferably ridges [700] are thermoformed directly on the surface of the posterior sheets, but they may be comprised of any materials and formed by any process, such as elastic materials like silicone, rubber, or flexible plastic adhered to the surface of the posterior sheets using a high frequency welding process or the like. Ridges [700] comprised of an elastic material adhered to the surface improve efficiency of the device by mimicking massage motions even with partial inflation of the bladders.

FIG. 11 is a plan view of a breast pad with topological shading to show how the ridges may be formed. Ridges [700] that are thermoformed ensure partial inflation of the bladders, causing the bladders to inflate more quickly using the same amount of fluid compared to bladders without ridges. Ridges may be formed by one or more partially inflated subsectors of each fluid bladder sector, such as subsectors [5110] and [5111] of fluid bladder sector [511], subsectors [5120] and [5121] of fluid bladder sector [512], or subsectors [5130] and [5131] of fluid bladder sector [513]. These subsectors may also be delineated by partial seals, such as the seal [506]. In that case, because the seal [506] is subject to inflation pressures from both sides, its radius of curvature should be at least 10 mm.

Additional ridges, or bumps, may be added to the exterior of the partially inflated subsectors, such as [5112] and [5113]

on subsector [5110], and [5122] and [5123] on [512]. These additional bumps are arranged as an inner bump closer to the 'C' opening in the middle of the pads and an outer bump nearer the exterior edge, in order to mimic pressure that is exerted by the fingers in a manually performed breast massage. In particular, the outer bump should be higher than the inner bump. The optimal height of the inner bump is found to be in the range of 10 to 20 mm, and the optimal height of the outer bump is found to be in the range of 12 to 25 mm.

The bumps may be partially inflated and thermoformed or they may be flexible structures on the outside of the posterior sheets [502]. They further decrease the amount of pressure required to inflate the massage pads to result in sufficient breast massage effects. In the examples shown, before inflation, the volume of the first bladder [511] is approximately in the range of 10 ml to 25 ml, the volume of the second bladder [512] is approximately in the range of 10 ml to 25 ml, and the volume of the third bladder [513] is approximately in the range of 10 ml to 25 ml for both the smaller size pads and the larger size pads. After inflation, the total volume is in the range of 50-200 ml for the first bladder [511], 100-250 ml for the second bladder [512], and 75-250 ml for the third bladder [513]. For example, after inflation, the total volume of the first bladder could be 50 ml, the volume of the second bladder could be 100 ml and the volume of the third bladder 75 ml for the smallest size bladders and 200 ml, 250 ml and 250 ml respectively for the biggest size bladders.

Figure 8:
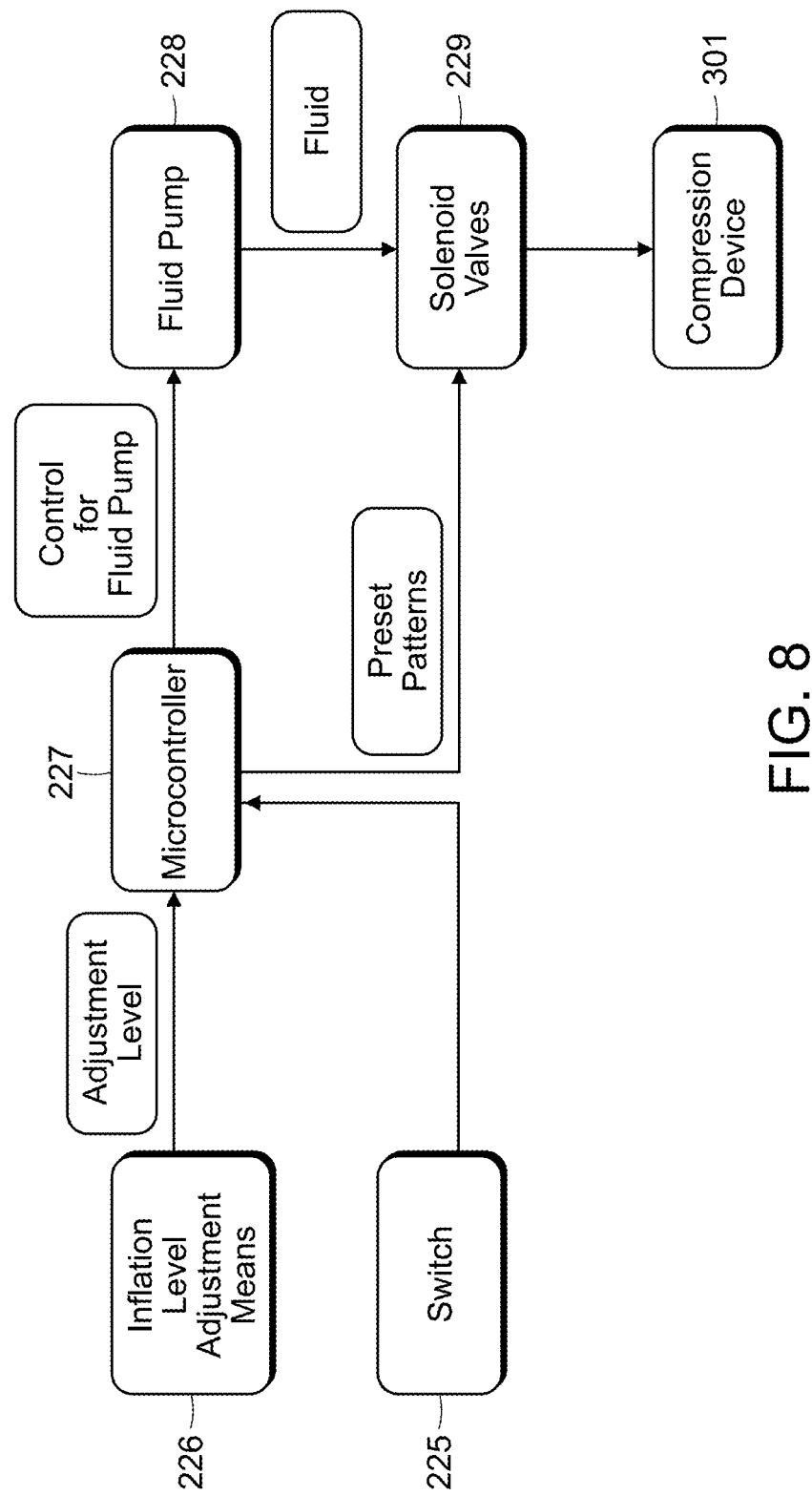
FIG. 8 is a high-level block diagram of the components operating the compression device.

With reference to FIG. 8, controller [402] comprises switch [225], inflation level adjustment means [226] to increase and decrease the inflation of bladders, microcontroller [227], fluid pump [228], and solenoid valves [229]. Switch [225] turns the device on or off by supplying or cutting off the supply of voltage. The inflation level adjustment means [226] may be adjustment buttons used to a) increase or decrease the pressure exerted by the compression device by increasing or decreasing the amount of the fluid pumped respectively and/or b) increase or decrease the duration for which the bladders inflate and deflate by increasing or decreasing the timing of the solenoid valves. The inflation level adjustment means [226] may be any mechanical means such as buttons or knobs for the user to increase or decrease the inflation level or frequency, said mechanical means in connection with a network of resistors which will adjust the voltage levels sent to the microcontroller [227]. Upon receiving these inflation settings for the bladders, microcontroller [227] controls the fluid pump [228] by adjusting the voltage required to power the pump. The source of the fluid used to inflate and deflate the bladders is the fluid pump [228]. The pump may be either hydraulic or an air pump depending on the nature of the fluid used in the system. The amount of fluid output by the pump [228] can be altered by altering the supply voltage of the pump. Microcontroller [227] controls both the fluid pump [228] and the solenoid valves [229]. Thus, microcontroller [227] can be programmed to inflate and deflate the bladders in different ways, for example, the bladders may be programmed to inflate and deflate in a rotational manner or they can be programmed to inflate and deflate simultaneously.

Solenoid valves [229] are electric valves that control the flow of fluid in and out of the bladders. Each solenoid valve may control two corresponding fluid bladder sectors of the left and right massage pads. When the valves [229] are turned on by the microcontroller [227], the fluid from the pump is sent to the compression device bladders via tubes [411-412; 421-423], causing the bladders [511-513; 521-523] to inflate. When the valves [229] are off, the fluid within the bladders is drained off from the solenoid valves, causing the bladders to deflate. By controlling these valves, the fluid supplied to the compression device can be turned on and off. The user can control the pressure exerted by the compression device by manipulating the inflation adjustment means [226].

Fluid may be introduced into the fluid bladders in a radial manner: for instance, fluid may be introduced into the first fluid bladder sector [511] until it is fully inflated, then into the second [512], followed by the third [513]. This method of introducing fluid into the fluid bladders results in a radial massage around the breast. The same radial massage can also be achieved by inflating two fluid bladder sectors at a time, for instance, the first and second sectors, followed by the second and third, followed by the third and the first. Fluid may also be introduced into fluid bladder sectors that are diametrically opposite to each other, particular in the case where there are four or more fluid bladders.

Figure 12:
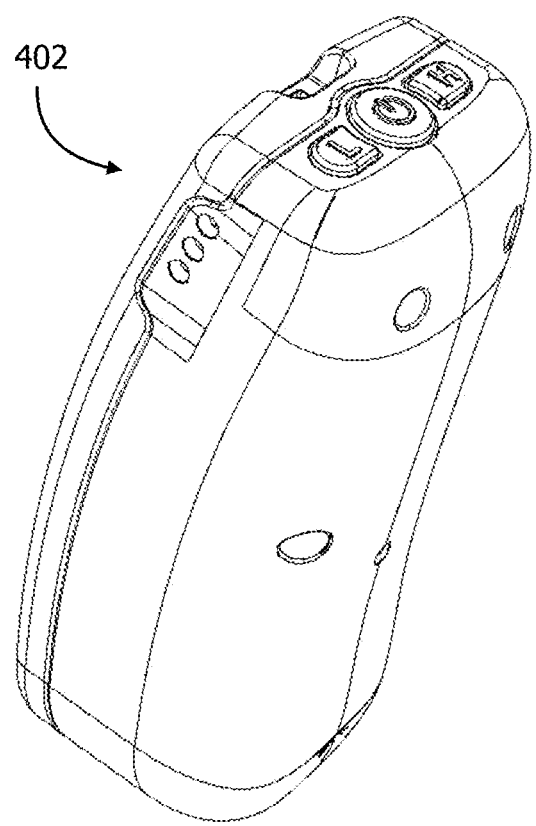
FIG. 12 is a perspective view of a controller.

Controller [402] as shown in FIG. 12 is a hand-held controller with a curved surface so that the controller is ergonomical and when placed in holster [109], the controller fits within holster [109] and rests comfortably against the breastbone or the sternum. Thus, controller [402] may comprise an outer casing with a curved surface such that the controller resembles a torus sector in shape. The volume of the bladders of the breast pads may allow for the use of a fluid pump capable of outputting 1-3 L/min with force of the fluid in the range of 50-150 KPa. Such a pump may be small enough to fit within an 80 cubic cm volume. The ergonomic, curved shape of the controller and the size of the pump allow for the controller to be small enough to fit inside the holster [109] of the bra and rest against the sternum without user discomfort. In addition, the shape of the controller and its close fit against the breastbone or sternum may also act as an additional support to the breast pads by offering resistance to the bladder and restricting them from inflating outward (away from the breasts), thereby increasing the effectiveness of massage in the cleavage region.

Given the design of the C-shaped pads that maximize coverage over the surface of the breast, and ridges that reduce the amount of inflation needed to result in effective massage, the power requirements to inflate the fluid bladders are minimal. During inflation, the pressure inside each bladders is within the range of 50-150 KPa, and the maximum force exerted by each bladder on the surface of each breast is in the range of 2.00-7.50 KgF by the first bladder [511], 2.0-7.50 KgF by the second bladder [512] and 2.00-7.50 KgF by the third bladder [513].

As can be seen in FIG. 6, breast pads [301(L)] and [301(R)] are each formed into a frustum shape when closed by closure means [305; 306]. The C-shape of breast pads enables size-adjustability of the breast pad, as adjusting the closure means adjusts the central angle of the frustum which allows the breast pads to conform to various breast sizes and shapes. Closure means [305; 306] such as buttons, snaps, Velcro, or their equivalents, would all be suitable for adjustable fastening. The seals [503] between bladders provide additional bending points to the bladder to increase ease of conforming to different breast sizes and shapes. This C-shape with size-adjustability allows the breast pad to fit comfortably over different sized breasts. In addition, the breast pads may be produced multiple sizes to fit a broader range of breast shapes and sizes; for instance, a small size (S) breast pad may fit breast sizes ranging from 30 to 34 and cup sizes ranging from A to C, a medium size (M) breast pad may fit breast sizes ranging from 34 to 38 and cup sizes ranging from C to FF, a large size (L) breast pad may fit breast sizes ranging from 38 to 42 and cup sizes ranging from A to FF. These sizes are for illustrative purposes only.

Figure 9:
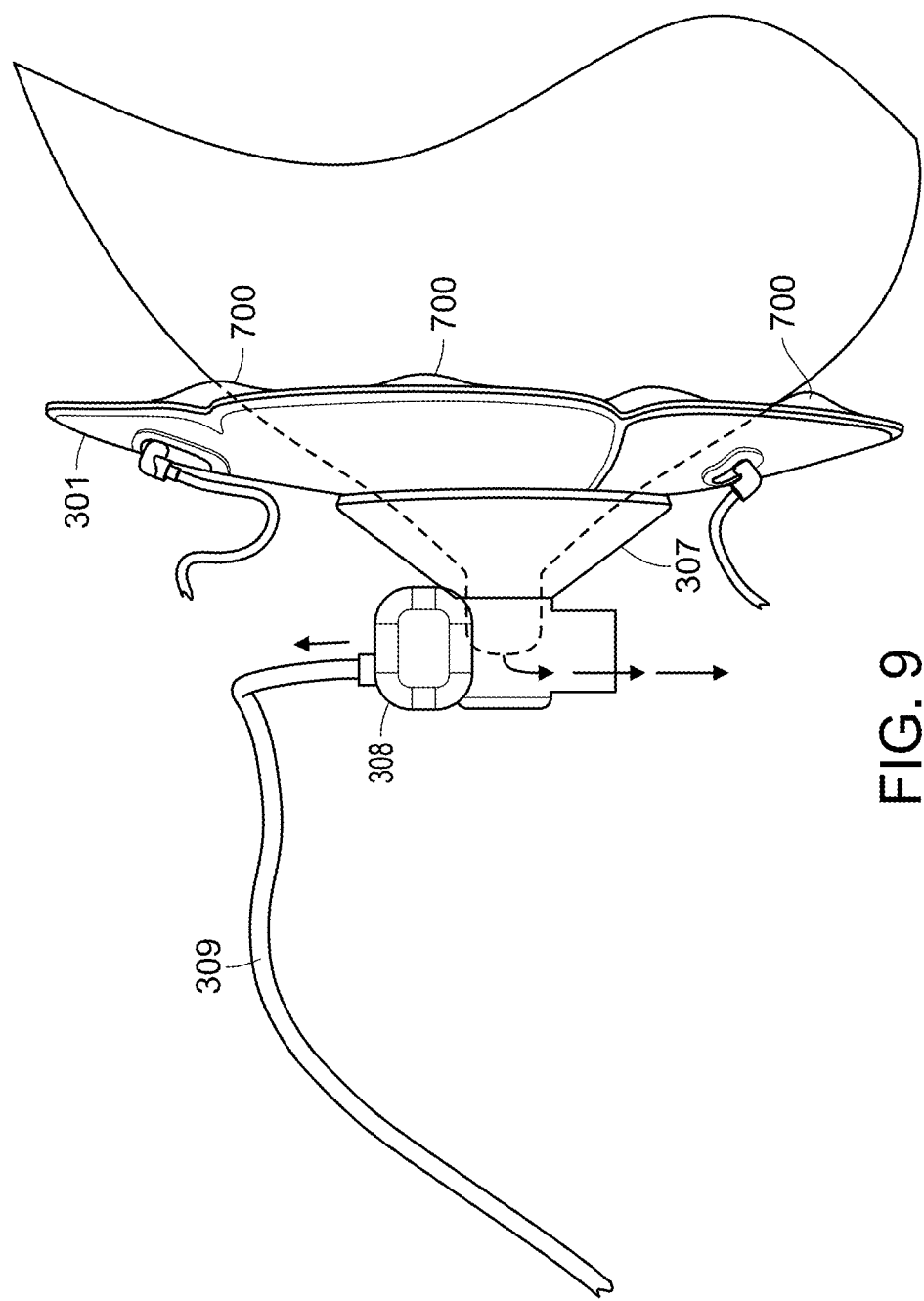
FIG. 9 is a side view of the compression device as it would lay on a user's breast, when used in combination with a breast pump.

When closed, each breast pads forms an opening [601 or 602] at the upper part of the frustum, through which a breast pump flange of any size [701] can be accepted. By allowing the breast pump flange [701] to lay directly against the breast, a tight seal is formed between the breast pump and the breast. FIG. 9 is a side view of the compression device [301] and breast pump [308] atop a user's breast. Ridges [700] face the breast so that when the bladders inflate and deflate in a rotational manner, the ridges [700] apply pressure to the breast. FIG. 9 illustrates the placement of the nipple into the flange [307]. As air is suctioned out into an air tube [309], milk is expressed and collected into a milk storage unit in the direction shown.

Figure 2:
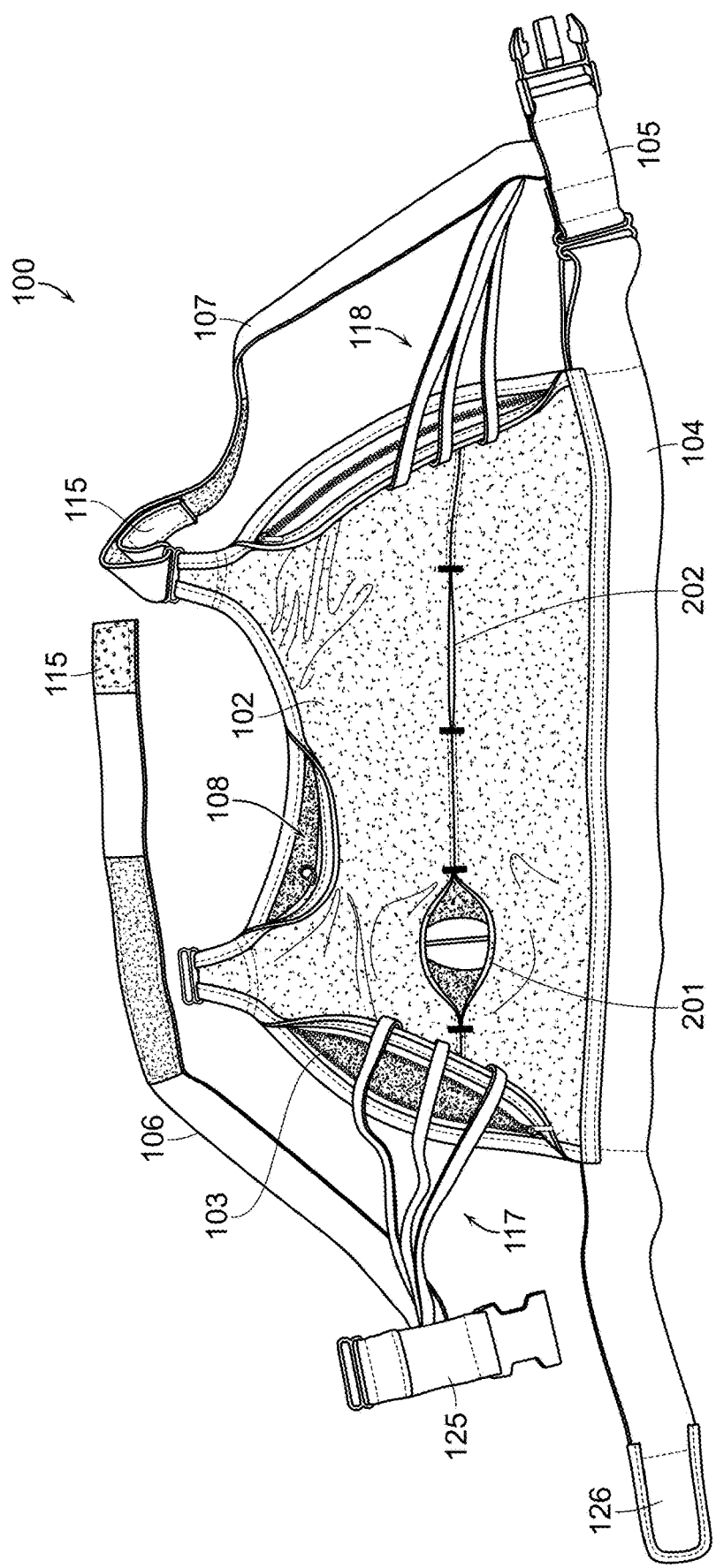
FIG. 2 is a posterior view of the garment.
Figure 3:
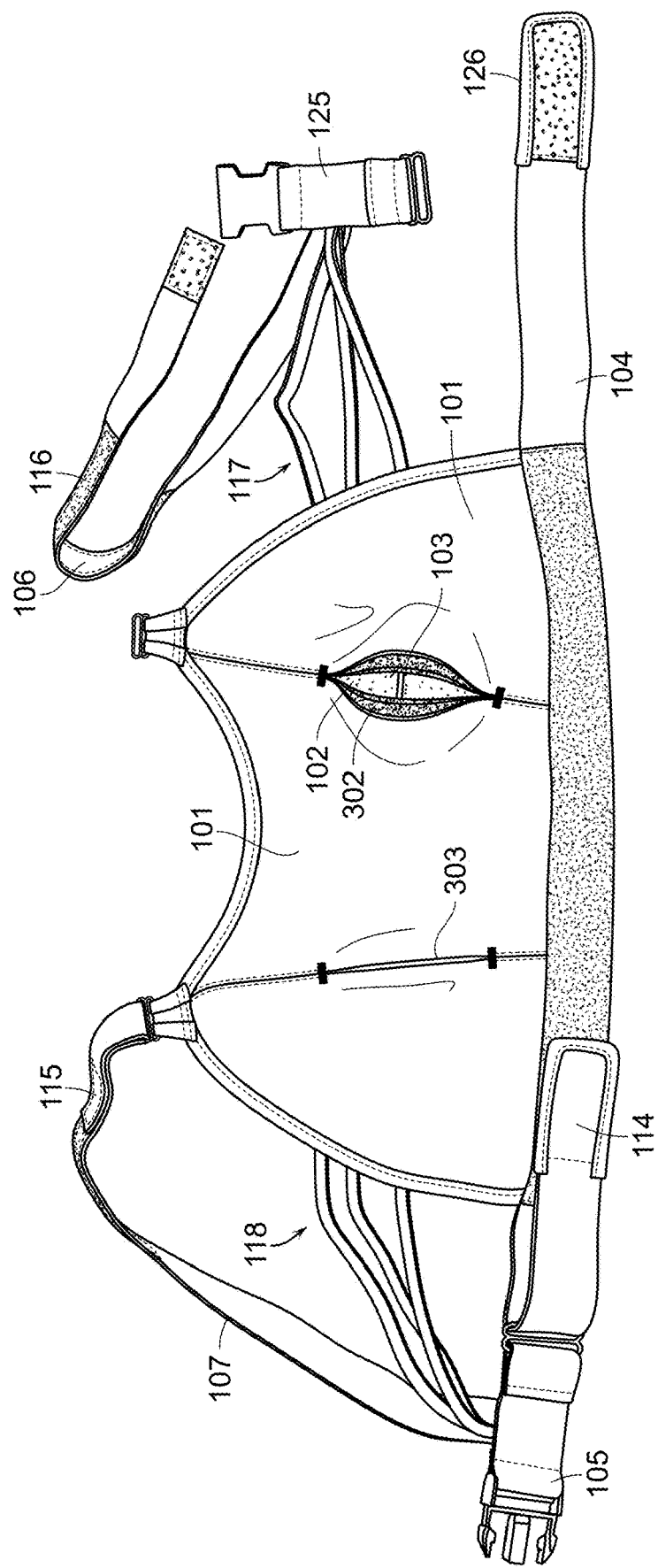
FIG. 3 is an anterior view of the garment.

As can be seen in FIG. 2 and FIG. 3, garment inner layer [102] comprises a horizontal opening [201; 202] in the area of each nipple, while outer layer [101] and compression layer [103] each comprise vertical openings [302; 303] in the area of each nipple. The positioning of said openings facilitate the easy attachment of the breast pump flange to the breast. The shape of said openings alternating between horizontal and vertical positioning furthermore ensures that the flange is held snugly in place without moving. Small cuts made on the seals of the compression pads further facilitate the attachment and compatibility with breast pump flanges of different sizes and allows for breast flanges to be inserted from either the front or back.

Figure 10:
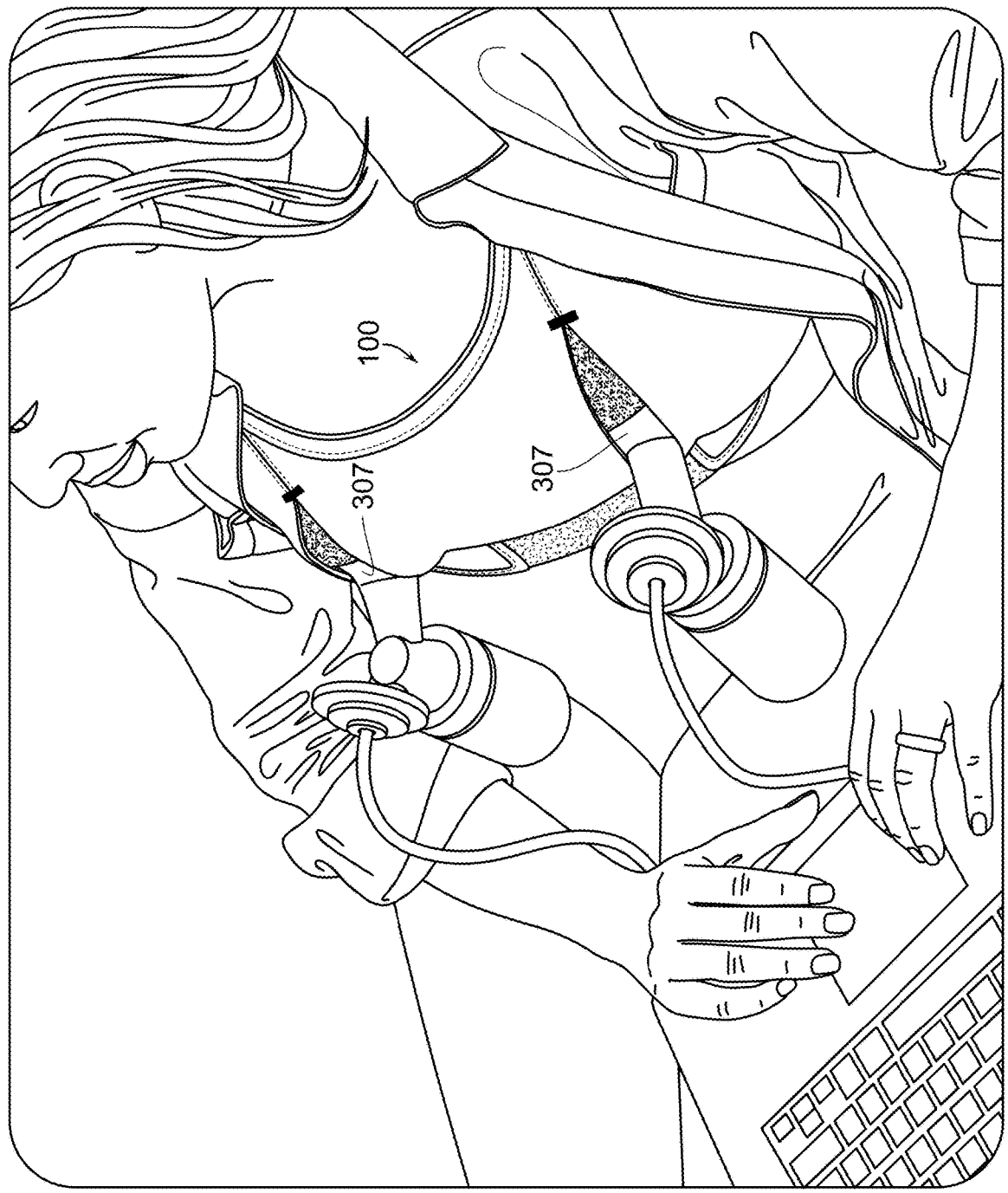
FIG. 10 is a depiction of environmental use of the garment, the compression device, and a breast pump.

Similarly, it is important that breast pads [301(L); 301(R)] stay in place without shifting, and even more important that they expand inward towards the breast when inflated. Thus, compression layer is comprised of a material with low elasticity such as Neoprene fabric or Fabric backed Foam. Moreover, holster [109] is located on compression layer centered between the breasts, so that the breast pads are further kept in place by the controller [402] and the controller becomes an additional barrier against which the bladders can push so as to provide adequate massage in the cleavage area of the breast. Further, the breast pads may be held firmly in place by the use of fastening mechanisms like Velcro added into the compression layer. Holster [109] lends added convenience to the device, as the breast pads and controller all conveniently rest within pocket [108]. Closure means [110; 111] allow the user to close the pocket [108] and wear while pumping, as depicted in FIG. 10. Closure means [110; 111] are depicted as buttons in FIG. 1, but may be any other types of closure devices such as Velcro or zippers. Side zippers [112; 113] provide easy access to the breast pads while inside of the garment, so that they do not need to be removed or rearranged from the top of the pocket.

Adjustability is an important feature of the garment, because it ensures a proper fit, crucial to keeping the breast pads in place so that they expand inward towards the breast as designed. For instance, torso band [104] comprises closure means [105] and an adjustable Velcro strap [114]. Here, closure means [105] is a side release plastic buckle, but any other sturdy closure means may be used. Left [106] and right [107] shoulder straps are preferably also adjustable, here shown using foldover Velcro straps [115; 116]. Elastic side straps [117; 118] also hold the bust section of the garment closer against the body while worn, further ensuring that the breast pads stay in place.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention as defined by the following claims.

The invention claimed is:

1. An inflatable breast massage cushion for hands-free compression during nursing comprising:
    an inner sheet and an outer sheet sealed together forming a C-shaped pad, wherein the inner sheet and the outer sheet are sealed together at an inner circumference of the C-shaped pad, an outer circumference of the C-shaped pad, and along an entire length of at least two radii of the C-shaped pad, thereby forming at least three fluid bladder sectors, wherein the inner sheet and the outer sheet are sealed together with seals having a width between 2.5 mm and 3 mm,
    a fluid egress opening serving each of the fluid bladder sectors; and
    a connection means for adjustably connecting the ends of the C-shaped pad together such that the pad forms a frustum for placement over a breast, the frustum having an angle that is adjustable by said connection means.

2. The inflatable breast massage cushion of claim 1 wherein a radius of curvature of any edge of the C-shaped pad is between 2.5 mm and 3.5 mm.

3. The inflatable breast massage cushion of claim 2 wherein each fluid bladder sector is further subdivided into one or more subsectors formed by one or more partially inflated ridges on the inner sheet.

4. The inflatable breast massage cushion of claim 3 wherein each subsector comprises an inner ridge and an outer ridge, wherein the outer ridge height is greater than that of the inner ridge height.

5. The inflatable breast massage cushion of claim 1 wherein each fluid bladder sector is further subdivided into one or more subsectors formed by one or more partially inflated ridges on the inner sheet.

6. The inflatable breast massage cushion of claim 5 wherein each subsector comprises an inner ridge and an outer ridge, wherein the outer ridge height is greater than that of the inner ridge height.

7. An automated nursing system comprising:
    a left breast pad and a right breast pad, each breast pad comprising
        an inner sheet and an outer sheet sealed together forming a C-shaped pad, wherein the inner sheet and the outer sheet are sealed together at an inner circumference of the C-shaped pad, an outer circumference of the C-shaped pad, and along an entire length of at least two radii of the C-shaped pad, thereby forming at least three fluid bladder sectors, wherein the inner sheet and the outer sheet are sealed together with seals having a width between 2.5 mm and 3 mm,
        a fluid egress opening serving each of the fluid bladder sectors; and a connection means for adjustably connecting the ends of the C-shaped pad together such that the pad forms a frustum for placement over a breast, the frustum having an angle that is adjustable by said connection means; and a massage controller comprising an electric pump and a plurality of solenoid valves connected to each fluid supply tube.

8. The automated nursing system of claim 7 further comprising a nursing garment comprising an inner layer and a compression layer, the inner layer and the compression layer forming a pocket for receiving the left breast pad and the right breast pad, and the compression layer further comprising a holster for receiving the massage controller, and wherein the compression layer is comprised of a lower elasticity material than the inner layer whereby the left breast pad and right breast pad inflate towards the inner layer.

9. The automated nursing system of claim 8 wherein the massage controller fits within the holster and comprises a curved surface such that the massage controller is substantially torus sector-shaped, whereby when placed within the holster the massage controller may align with a user's sternum.

* * * * *